United States Patent [19]

Wells

[11] Patent Number: 4,952,359

[45] Date of Patent: Aug. 28, 1990

[54] METHOD FOR MAKING SPLITTABLE CATHETER

[75] Inventor: Stanley C. Wells, Centerville, Ohio

[73] Assignee: Becton, Dickinson and Company, Franklin Lakes, N.J.

[21] Appl. No.: 227,040

[22] Filed: Aug. 1, 1988

Related U.S. Application Data

[62] Division of Ser. No. 11,783, Feb. 6, 1987, Pat. No. 4,776,846.

[51] Int. Cl.[5] ............................................. B29C 47/06
[52] U.S. Cl. .................................... 264/139; 264/146; 264/150; 264/173; 425/133.1
[58] Field of Search ............... 264/146, 150, 173, 139; 425/133.1, 131.1

[56] References Cited

U.S. PATENT DOCUMENTS

| | | | |
|---|---|---|---|
| 3,619,395 | 11/1971 | Skendzic | 264/173 |
| 3,677,243 | 7/1972 | Nerz | 128/214.4 |
| 3,752,617 | 8/1973 | Burlis et al. | 425/131.1 |
| 3,853,130 | 12/1974 | Sheridan | 128/349 |
| 4,054,136 | 10/1977 | von Zeppelin | 128/214.4 |
| 4,229,407 | 10/1980 | Craig | 264/519 |
| 4,296,157 | 10/1981 | Conti | 264/173 |
| 4,330,497 | 5/1982 | Agdanowski | 264/150 |
| 4,402,685 | 9/1983 | Buhler et al. | 604/280 |
| 4,412,832 | 11/1983 | Kling et al. | 604/164 |
| 4,451,256 | 5/1984 | Weikl et al. | 604/164 |
| 4,471,778 | 9/1984 | Toye | 128/305.3 |

FOREIGN PATENT DOCUMENTS 2104226 12/1971 Fed. Rep. of Germany.

*Primary Examiner*—Jeffery Thurlow
*Attorney, Agent, or Firm*—Robert P. Grindle

[57] ABSTRACT

A method is provided for making a splittable introducer catheter by co-extruding two different polymers of differing solubilities, so that v-shaped strips are formed on each side of the catheter wall which may be easily stripped from the main catheter tube. This leaves an introducer catheter which is easily split along the narrowed v-shaped grooves on diametrically opposite walls of the catheter.

3 Claims, 2 Drawing Sheets

METHOD FOR MAKING SPLITTABLE CATHETER

This is a division of application Ser. No. 011,783, filed Feb. 6, 1987, now U.S. Pat. No. 4,776,846 issued 10-11-88.

BACKGROUND OF THE DISCLOSURE

This relates to splittable catheters used in connection with aiding insertion of long-line catheters into a human body. The technique of the preferred arrangement for inserting a long-line catheter includes making the venipuncture with a hollow needle that carries coaxially thereover a splittable placement catheter. Once the vein has been penetrated and blood is visible in the flashback chamber, the needle and flashback chamber are removed leaving the placement catheter through the site of the puncture and in the vein. A long-line catheter or guidewire is threaded through the placed catheter and thereafter the catheter is removed from the vein leaving the guidewire or the long-line catheter in place. The removed placement catheter is designed to split longitudinally so that same can be taken away from the guidewire or the long-line catheter without difficulty.

A variety of approaches have been disclosed for facilitating the longitudinal split of the placement catheter. For example, the Boarini et al U.S. Pat. No. 4,411,654 shows various catheter cross sectional configurations including rupture lines produced by mechanically scoring the catheter tube or preferably by placing same in the tube during extrusion. Fabrication of each cross sectional configuration is very difficult since polymer materials have a memory and therefore tend to knit (extrusion) or split (scoring).

The rupture lines are provided to produce a uniform weakness in the catheter tube assisting smooth longitudinal tearing of the tube during removal. It has also been suggested to provide rupture lines by use of oriented polymer material formed by extrusion. In addition to the scoring, the rupture line of weakness could be merely an opening or lumen extending through the length of the wall of the tubing. The Buhler et al U.S. Pat. No. 4,402,685 discloses an incompatible polymer simultaneously extruded with a base polymer to form two semi-circular walls which are joined to two strips of the simultaneously extruded modified polymer. The strips are located 180° apart such that the catheter tube is readily divided by tearing the juncture between the base polymer and the modified polymer.

German Patent No. 2,104,226 discloses a short catheter polymeric tube having longitudinal tear lines or fracture points produced by molding or machining a preformed polymeric tube with a uniform wall thickness such that the tearing or ripping is a function of the residual wall thickness at the tear line. The Osborne U.S. Pat. No. 4,306,562 discloses a splittable catheter having a tubular structure formed of a flexible material with physical properties of molecular orientation thus promoting longitudinal tearing along the length of the tubular structure. More specifically, Teflon is a preferred material because it can be longitudinally oriented through extrusion.

Finally, the Kling et al U.S. Pat. No. 4,412,832 shows a catheter tube of a semi-rigid material which is beveled at the distal end and scored longitudinally in one or more places to provide lines along which the catheter tube may be split or peeled apart.

Therefore, it is of concern with respect to the prior devices as to the process used and physical nature of the weakened area. That is to say that, the two main problems are the ease of manufacture without additional operating steps and the accuracy of producing the thinned area as a consequence of the forming process. Weakness beyond that required for splitting can cause failure during insertion particularly in the area of the tip of the catheter where the material is thinned to help insertion.

It is the object of this invention to show an extremely high strength material which allows requisite circumferential stress resistance even though areas of weakness extend from the tip of the catheter longitudinally up the catheter body.

It is still further an object of the present placement catheter of the splittable type to show a stripe composition and shape which defines the cross-sectional configuration of the area for the longitudinal line of weakness.

It is an object to teach a way in which a relatively sharp V-shaped line of weakness can be generated longitudinally along the body of the thin-walled polyurethane catheter having high circumferential or hoop strength transverse to the V-shaped groove but having relatively low shear tear strength along the line of the sharp inward point or bottom of the line of weakness. Consistent with the foregoing objects and in order to overcome the problems besetting the prior patent art, the disclosure herein teaches the preferred process method and resulting structure.

SUMMARY OF THE DISCLOSURE

The cross sectional area of the splittable polymeric catheter of the present invention is uniform in thickness and circular in configuration. There are lines of weakness, however, established therein by means of co-extrusion of a poorly adhering striped portion on several sides of the surface of the body of the catheter. In the preferred embodiment, there are two such stripes located on the outside surface across from one another. Each has a cross sectional configuration that is generally V-shaped thus forming a residual portion of substantially reduced radial thickness, in the cross section, of the catheter body. During production the co-extrusion of the base polymer and the striped polymer form a completely uniform thickness in a circular configuration which provides the necessary and convenient splittable catheter tubular construction required for site placement of the splittable catheter. More specifically, the catheter is carried over a needle and inserted by means of venipuncture and flashback. The needle and flashback chamber being removed leaves the splittable placement catheter of the present invention disposed within the patient's vein. Through this placement catheter can be inserted a long-line catheter or a guidewire.

Subsequent to insertion of the long-line catheter or guidewire, the splittable catheter may be removed from the patient by pulling same axially outwardly along the guidewire or long-line catheter. The lines of weakness formed after co-extrusion of the base material and the striped filler material are the result of removal of the striped portion. The splittable catheter can be easily separated along those surfaces and removed from about the guidewire or long-line catheter. The striped material is easily removed during manufacture so that the remaining base material or catheter body is easily split along the remaining line(s) of weakness.

The V-shaped groove formed by removal of the striped material portion prevents the groove from swelling during the exit of the co-extrusion from the extrusion die. Without a filler stripe, swelling would essentially remove the sharp point or line of weakness at the bottom of the V-shaped groove leaving only a rounded filet which would make the splitting of the catheter much more difficult. Control of the thickness of the residual base material would be inconsistent without a filler stripe. Tests with an extrusion die having a knife or cutting point to score a groove result in a tube with a surface having only a rounded notch. The reason for this is that the memory in polymeric material causes it to swell upon release of the pressure once it has exited the extrusion die. The resulting extrusion has knitted over the cut line. Scoring made in a subsequent operation of the full formed tube requires removal of the cut material and accurate control of the cut depth. These are very difficult to do in a small diameter flexible polymeric tube.

The method of manufacturing the preferred splittable placement catheter includes the process of simultaneously co-extruding the cross section of the catheter body having at least one area of reduced cross sectional wall thickness and the striped material to fill this area of decreased thickness to prevent die swelling into the area for reduced thickness. The resulting cross section of both has a uniform thickness throughout and a substantially circular shape. As part of the process, the stripe forming material that is co-extruded is then removed leaving an uncut, clean and smooth area of longitudinal weakness which can be split without difficulty. The result of this technique leaves a particulate-free surface of a generally "V" shape about the area of weakness. This is extremely important in connection with a catheter to be placed in the human body. The thickness of the residual base material under the "V" is accurately maintained.

In addition and as already explained, the removed striped material leaves a sharp edge to the bottom of the V-shaped groove aiding in the longitudinal splitting of the catheter along the line of the bottom of the V-shaped groove. In one preferred arrangement, the stripe material is an olefinic polymer and the main body of the tube is a polyurethane. Other striped polymers can be used to facilitate removal. Polyurethane polymers are extremely biocompatible and strong.

DETAILED DESCRIPTION OF THE DRAWINGS

Figure 1:
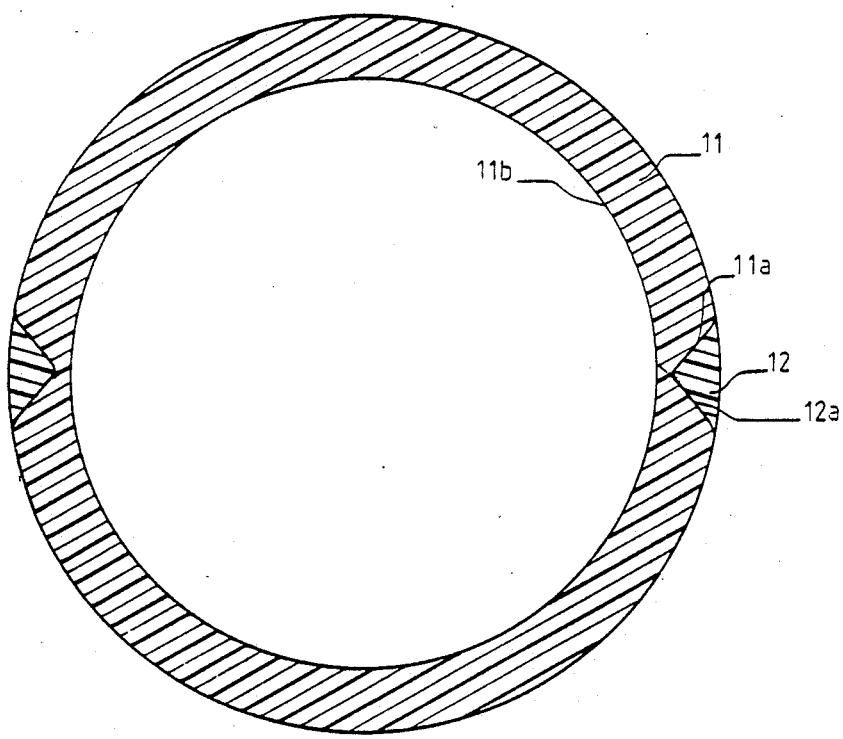
FIG. 1 shows the cross section of a splittable placement catheter wherein the striped material and the base material are both intact.
Figure 2:
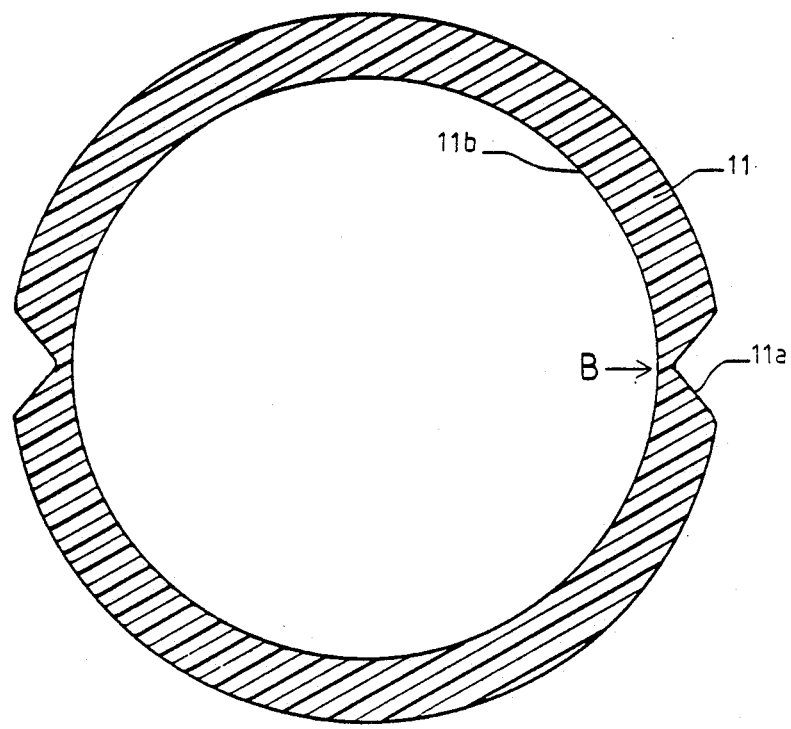
FIG. 2 shows the cross section of a splittable placement catheter wherein the striped material has been removed.
Figure 3:
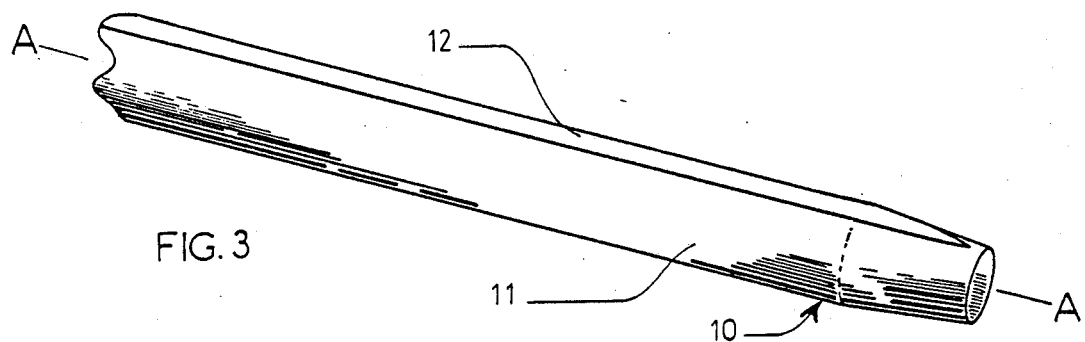
FIG. 3 shows a partial perspective view of the placement catheter showing the manner in which stripe material is set into the side and extends toward the tip.

In FIG. 1, a cross sectional view has been taken as would be seen from the plane normal to axis AA of FIG. 3. More specifically, the catheter 10 includes a body portion 11 and a stripe material portion 12 each of which combine to form the uniform circular thickness in the cross sectional view. The body portion is made by co-extrusion with the stripe material portion 12 in a combining extrusion die block. The body portion 11 is in the preferred embodiment Vialon ® polyurethane, a product of Deseret Medical, Inc., Sandy, Utah, but other polyurethanes and polymers normally used for catheters will work. The stripe material portion 12 may be any olefinic material such as and only by way of example, the polyethylene made by El Paso Chemical. These materials are co-extruded through a specially-designed die which lays the two together and forms a surface therebetween, i.e. surface 11a and the body portion 11 and surface 12a on the stripe material portion 12. The process conditions for the co-extrusion including melting polyurethane polymer of the body in the temperature range of 190° to 210° C. and the olefinic polyethylene polymer of the stripe portion 12 at a temperature of about 180° to 200° C. and then co-extruding the two together to form simultaneously a catheter body wall thickness of approximately 0.007 to 0.011 inches for a 13 to 14 gauge catheter tube with a residual thinned portion B extending from the inside wall of 11b of the catheter 11 in FIGS. 1 and 2 of approximately 0.003 to 0.006 inches. It has been found that the residual thinned portion B is easily split and permits convenient removal of the placement catheter 10 from any guidewire or long-line catheter placed therethrough, notwithstanding the tear strength of Vialon ® polyurethane. The specific Vialon ® polyurethane polymer for the preferred embodiment has the following physical characteristics: tensile strength of 6000 psi, 25% modulus 2,000±200 psi, Shore D hardness 65±4, minimum tear strength based upon American Society for Testing and Materials Die C specifications of 722 pli (pounds per linear inch) average. The tear strength of the polyurethane is obtained from an extruded film from which an ASTM Die C configuration sample was stamped out and Instron tested per ASTM specifications.

Polyurethane as the resin for the body 11 is ideal not only because of its biocompatibility, but its great resistance to kinking which is extremely important in connection with a relatively long catheter having a thin wall and a small outer diameter particularly in view of the final configuration wherein there is a line of weakness. In addition to its ability to resist kinking, the tip which is thinned to provide a penetrating tip for ease of insertion in an about-the-needle technique has to maintain its integrity even though the body 11 has a split extending almost all the way to the end of the tip. Polyurethane catheters show excellent but easily controlled tear resistance even at the thinned tip and consequently prevent a serious problem called peel-back wherein the tip mushrooms or curls back on itself and prevents insertion or fractures leaving particles in the site of the puncture through the human body. Considerable force is applied to the tip of the catheter as same is forced in through the human skin while same is carried about the needle which initially punctures the skin. Sufficient hoop or circumferential strength is required in order to prevent the catheter tip from prematurely failing during insertion. Because of the process and the material selected, i.e., polyurethane in co-extrusion, the tear resistance of the weakened catheter tubing is excellent although it will tear well longitudinally when necessary but has excellent integrity until such time as the tear or split is required. This is due primarily to the elastomeric nature of the polyurethane polymer and the structure arrangement where thinned portion B is about the same thickness as the bulk of the tip. Circumferential or hoop strength is also essential to prevent premature splitting due to flattening or kinking of the tubing during handling. That type of flexure has a tendency to cause materials with less overall strength than polyurethane to fail across the area of weakness.

FIG. 2 shows the enlarged cross section of catheter wherein the stripe material portion 12 has been removed. A careful examination of the surface 11a which remains after the filler portion has been removed shows same to be smooth as a consequence of the co-extrusion process. While the figures are patent draftsmen's drawings in accordance with the requirements of the United States Patent Office, they were made from microscopic photographs and show the results of actual extrusion as accurately as possible with pen and ink. More importantly, the surface 11a is entirely free of particulate matter or debris. This cleanliness is critical to the performance of the catheter in a venipuncture as such surface defects are detrimental to the proper use of the product not only from a physical structure standpoint, but also with regard to safety. With regard to the former, the stress concentrations along a porous surface would tend to cause premature failure and in connection with the latter, debris or particulate matter cannot be tolerated in a product to be inserted into a patient. Similarly, a rough surface on the catheter is irritating upon placement and in use.

Figure 4:
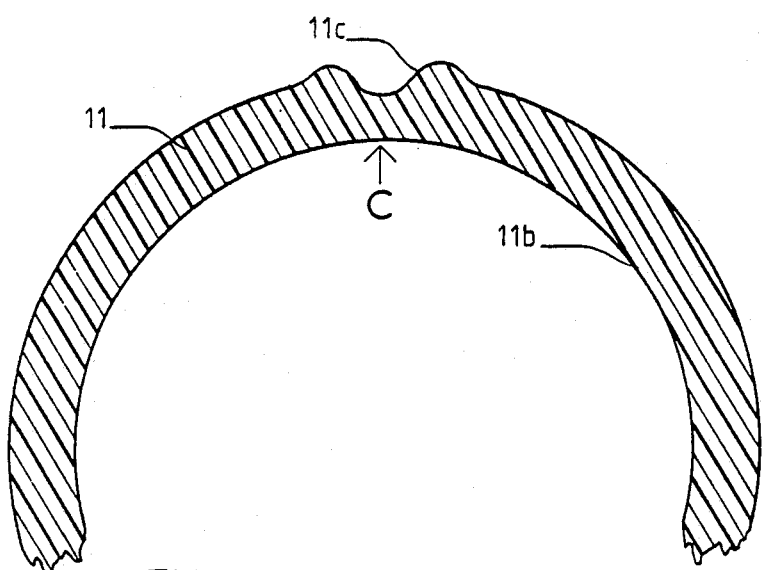
FIG. 4 illustrates the tube formed with an extrusion die having a "V" shaped knife and the rounded shape of the groove due to die swelling.

As illustrated in FIG. 4, the preferred catheter is made of polyurethane which is a highly viscoelastic material and will act to resist forming a sharp or clearcut line of weakness. This is so because the material, if co-extruded through a die having portions designed to provide the V-shaped grooves, will not give a sharp line due to the fact that the memory of the material will cause same to swell in area 11c upon exit from the extrusion die and thus virtually wipe out the desired shape. More detrimental is what happens to the thinned portion C remaining. Same is thick because of swelling. Cutting deeper will not work as the results are variable and inconsistent Consequently, a satisfactory product with appropriate lines of weakness would be very difficult to make unless the co-extrusion of a stripe material portion is added to keep the groove for the line of weakness from knitting over. The only other way in which a catheter of this type could be made is to extrude the tubing and cut same with a razor. This is very difficult in that the tubing is extremely thin-walled and of small outside diameter. These two parameters of the tubing cause serious handling problems resulting in concerns as to ability to continuously and repeatedly form a cut of a specific depth without cutting all the way through or without cutting an inadequate amount. Moreover, the ability to handle this tube during the cutting process, i.e. support position and control would also be nearly impossible.

The release mechanism of the preferred striped material portion 12 is based on the difference in the solubility parameter of the polyolefin resin of the striped material portion 12 and the polyurethane material for the body 11. While a specific solubility parameter is not required, the resins or polymers selected for the stripe and body must be such that there is a difference. The actual force required is a function of geometry and materials used. In the preferred arrangement, the tear force to split the stripe 12 from catheter 11 should be in the range of 0.30 to 0.60 pounds and it should be appreciated that the tear force that is across the molded tip of the catheter will be slightly different as a consequence of the thinning of the material portion 12 at the tip area. The tip is short in length and has a much thinner wall than the main body of the catheter tube except in thinned portion B.

Those skilled in the polymer arts will appreciate that the stripe material can be selected from polymeric substances which are soluble in a suitable solvent. Removal of the strip can for example take place in the quench tanks following extrusion. These tanks usually contain tap water at room temperature or tap temperature. A typical system has a drain and makeup pipe scheme whereby the water is constantly renewed and the temperature maintained. Polymers for the stripe such as ethylene vinyl alcohol (EVOH), or the like are useful since they are dissolved in water. A balance of the water coolant temperature, time in the tank and solubility of the polymer is important to this technique. Another approach to easy removal of stripe 12 is to use a water soluble polymer such as polyethyloxazoline as the stripe portion of the co-extrusion. The tubing is passed through a cooling tank usually having water. That step can be used to dissolve the stripe 12 while at the same time setting the preferred configuration for the catheter 11. The polymer-solvent interaction parameter is a semiempirical "constant" which provides a measure of the solvent power of a given liquid for a polymer. It continues to play a valuable role in the quantitative description of properties of polymer solutions and gels, even though its numerical value in a given polymer-solvent system usually depends on the ratio of the two components and on temperature. Consequently, any solvent can be used and the rate at which the stripe 12 dissolves is a function of the materials selected, agitation, etc. Temperature is only a factor to the extent that cooling is required.

While specific examples have been shown and described, the invention in its broadest context should be understood from the claims which follow. Those skilled in the art will no doubt appreciate that other materials and combinations can be used as a substitute for those specifically mentioned herein, and it is the object of the claims to define those as well.

Such aforementioned tubing could be employed in conjunction with and joined to an adaptor piece, said adaptor being molded from a plastic or elastomer, in which its chemical nature is such that a strong bond can be made between tubing and adaptor by any number of conventional means such as solvents, heat, RF, ultrasonics, dielectric bonding. Design features are incorporated in the adaptor in such a way that weak areas are molded longitudinally (in the fluid flow direction) for the length of said adaptor. These weak areas are so placed in the distal end of the adaptor as to radially and axially line up with the weak areas of tubing, when joining techniques are used. The adaptor will also have some gripping means incorporated in its structure, to act as pull-tabs, where the splitting forces are applied to the subassembly.

Tear initiation of the subassembly starts near the proximal end of the adaptor by pulling tabs in opposite directions with both hands. The tear is perpetuated along the whole subassembly in the direction from proximal to distal ends by continued opposing pull of the hands until said subassembly becomes two distinctly separate parts.

While specific examples have been shown and described, the invention in its broadest context should be understood from the claims which follow. Those skilled in the art will no doubt appreciate that other materials and combinations can be used as a substitute for those specifically mentioned herein, and it is the object of the claims to define those as well.

What is claimed:

1. A method for producing a catheter assembly with a catheter configured to be readily split in half for ease of removal from insertion in a patient, said method comprising the steps of (a) simultaneously extruding a generally tubular catheter assembly with two diametrically formed v-shaped grooves formed therein, and v-shaped strips formed in said grooves, said generally tubular catheter being comprised of a different polymer from said strips;

said extruding step including (1) selecting in a first selecting step an elongated tubular body comprised of a first polymer;
   (2) said body being defined by a wall having a first radial cross-sectional thickness through the length thereof;
   (3) said wall having an inner surface and an outer surface;
   (4) the said inner surface of said wall defining a lumen extending centrally through the length of said body;
   (5) said wall having two diametrically opposed grooves therein;
   (6) each of said grooves having a continuously decreasing width in cross-section from said outer surface to form a v-shaped;
   (7) the bottom of each said v-shaped groove being at a point spaced from said inner surface of said wall;
   (8) said bottom of each said v-shaped groove cooperating with said inner surface of said wall to form a second radial cross-sectional thickness for said wall adjacent each of said diametrically opposed grooves;
   (9) selecting in a second selecting step a pair of strips;
   (10) said strips being v-shaped and the same size as said diametrically opposed grooves;
   (11) said strips being comprised of a second polymer different from said first polymer;
   (12) said first and second polymers having differing solubility parameters for promoting poor adhesion therebetween; and (b) stripping said strips from said v-shaped grooves for forming a catheter with a continuous tubular wall but readily split in half.

2. The method of claim 1 further comprising
   (a) said second areas of cross-sectional thickness are areas of uniform thickness providing preferential longitudinal tearing separation radially thereacross.

3. The method of claim 1, further comprising
   (a) said first selecting step including selecting polyurethane as said first polymer; and
   (b) said second selecting step including selecting polyethylene as said second polymer.

* * * * *